United States Patent [19]

Sawai et al.

[11] Patent Number: 5,211,956
[45] Date of Patent: May 18, 1993

[54] PHARMACEUTICAL COMPOSITIONS CONTAINING PHYTIC ACID OR ITS SALTS

[75] Inventors: Kiichi Sawai, Funabashi; Masayasu Kurono, Mie; Hiromoto Asai, Nagoya; Takahiko Mitani, Mie; Naohisa Ninomiya, Nagoya, all of Japan

[73] Assignee: Sanwa Kagaku Kenkyusho Co., Ltd., Aichi, Japan

[21] Appl. No.: 346,852

[22] Filed: May 3, 1989

[30] Foreign Application Priority Data

May 19, 1988 [JP] Japan ............... 63-122348
Nov. 22, 1988 [JP] Japan ............... 63-295167

[51] Int. Cl.$^5$ .................................. A61K 9/48
[52] U.S. Cl. ..................... 424/451; 424/464; 424/489
[58] Field of Search ............. 424/451, 464, 489

[56] References Cited

U.S. PATENT DOCUMENTS 4,758,430 7/1988 Sabin .................... 424/94.1

Primary Examiner—Thurman K. Page
Assistant Examiner—Leon R. Horne
Attorney, Agent, or Firm—Armstrong, Westerman, Hattori, McLeland & Naughton

[57] ABSTRACT

Pharmaceutical compositions for oral administration used for the treatment and prevention of hyperlipemia, obesity and obesity-related diseases contain phytic acid or its salt as a pharmaceutically effective component.

8 Claims, 1 Drawing Sheet

RESULTS OF INDUCTION-TESTING-WITH-TIME

CHANGES OF FREE FATTY ACIDS WITH CHANGES IN DOSAGES

RESULTS OF INDUCTION-TESTING-WITH-TIME

PHARMACEUTICAL COMPOSITIONS CONTAINING PHYTIC ACID OR ITS SALTS

BACKGROUND OF THE INVENTION

1. Field of the Invention

The present invention relates to a pharmaceutical composition for oral administration containing phytic acid or its salts, which is especially used for the treatment of hyperlipemia, obesity and obesity-related diseases.

2. Statement of the Prior Art

Hyperlipemia refers to diseases caused by abnormal increases in one or more of serum lipids, viz., cholesterol, triglyceride, phospholipid and free fatty acids and accompanied by various disorders.

Pathologies are generally broken down into Type IV induced by the cumulation of endogenous triglyceride, Type I induced by the cumulation of exogenous triglyceride, combined Type V thereof and the like.

Heretofore, various pharmaceutical compounds have been known for treating hyperlipemia. For instance, preparations based on clofibrate, dextran sulfate, nicotinic acid and the like have been known for Type IV hyperlipemia and hormone preparations such as progesterone and nicotic acid for Type V. However, although it has been reported that some amylase inhibitors are effective for Type I, no substantially effective pharmaceutical compounds have been reported at all.

As the remedies for obesity, on the other hand, there have known one type of drugs based on hormones, amino acids, inorganic substances, rutin and vitamins which are administrated directly to a living body to serve to promote the metabolism and decomposition of fats and another type of pharmaceutical compounds based on lactobacillus which serves to prevent in-vivo propagation of harmful bacteria, resulting in the intestinal absorption of nutrients such as amino acids and inorganic substances being promoted and intestinal disorders and metabolism being improved.

In expectation of an effect on restricted diets, treatments have been carried out with undigestible mannans or diet fibers, etc. which induce a feeling of fullness. However, since pharmaceutics having a decisive remedial effect have been found to tend to be strongly poisonous, there is still a demand for pharmaceutics administrable with high safety and great remedial effects.

Phytic acid is a compound which has been known for long and reported to promote the cultivation of lactobacillus (Japanese Patent Publication No. 39-72686) and stabilize vitamin C. The detoxication of bacteria by phytic acid has already been found by the present inventors (Japanese Patent Application No. 63-140385).

Phytic acids widely appear in plants as calcium and magnesium salts, sometimes a potassium salt. For instance, rice bran contains as high as 9.5 to 14.5% of phytic acid, and provides a starting material for commercial phytic acid and myoinositol deriving therefrom.

Phytic acid and its salt have been used in wide applications; in pharmaceutical applications, calcium phytate has been used as a calcium absorbefacient, rice bran itselt and sodium phytate as a preventive for calcium calculus, and potassium phytate for the treatment of hyper-calcemia and hyper-calciuria of sarcoidosis patients. They have also been utilized in various other fields as fermentative aids for brewing sake and wine, metal removers making use of the chelating action of phytic acid, antioxidants in the presence of iron and calcium ions and anticorrosives for metals.

However, it has not been reported that phytic acid and its salts may be effective as a preventive and remedy for hyperlipemia, esp., arteriosclerosis.

SUMMARY OF THE INVENTION

In view of the foregoing, the present invention has for its object to provide a pharmaceutical composition effective for the treatment and prevention of arteriosclerosis, esp., all the types of hyperlipemia including Type I.

Another object of the present invention is to provide a pharmaceutical composition for treating obesity and obesity-related diseases, which allows patients suffering from obesity, esp., functional obesity to lower their body weight without a lowering of their function and bodily strength and are also usable even by sound individuals.

The inventors have already discovered that when orally administrated in the process of nutrition experiments, phytic acid serves to reduce body smells, especially, foul breath, perspiratory smell and urinous smell. Further research studies of the effects of such removal has revealed that this is related to in-vivo metabolism, esp., the promotion of decomposition and metabolism of fats, leading to the accomplishment of the present invention. The present invention is characterized by the provision of a pharmaceutical composition containing phytic acid or its salts, which is effective for the remedy, treatment and prevention of hyperlipemia, obesity and obesity-related diseases.

It is here understood that the obesity-related diseases include fatty liver, diabetes and macromastia.

BRIEF DESCRIPTION OF THE DRAWINGS

The present invention will now be described with reference to the drawings, which are given for the purpose of illustration alone, and in which.

DETAILED EXPLANATION OF THE INVENTION

Figure 1:
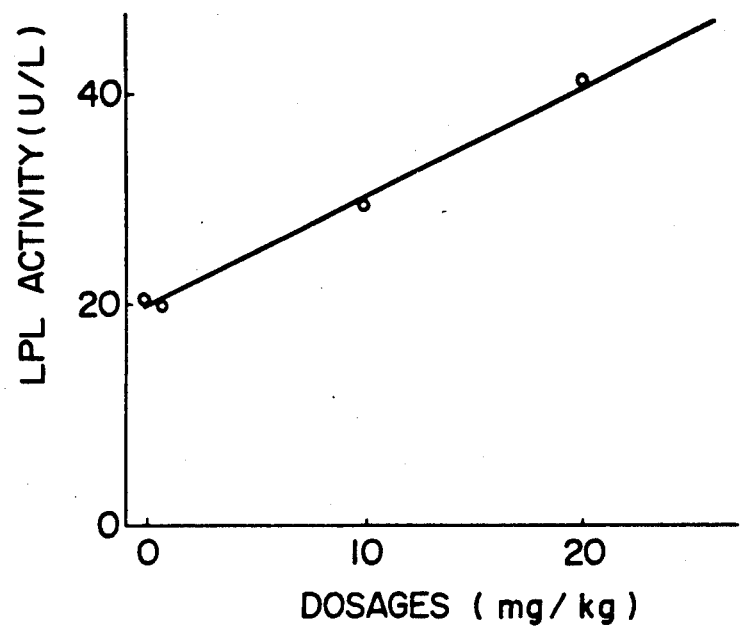
FIG. 1 is a graphical view illustrating changes of free fatty acids in blood with a change in the amount of phytic acid administrated.

As the salt of phytic acid, the most preference is given to an iron salt due to its increased effect. The iron salt of phytic acid is easily administrable by way of an oral route, and may be used in the form of powders or granules or mixed with food and drink by suitable means.

The phytates usable in the present invention may include non-toxic metal salts as well as non-toxic salts with organic salts, basic amino acids and organic ester residues such as, for instance, those represented by potassium phytate, sodium phytate, ammonium phytate, arginine phytate, ornithine phytate, lysine phytate, histidine phytate, monoethanolamine phytate, diethanolamine phytate, triethanolamine phytate and glucamine phytate.

A suitable dosage to humans, generally adults, of the compositions of the present invention, although varying depending upon conditions and types of preparations, is 1 to 100 mg/kg a day, as calculated in terms of phytic acids.

In various preparations, phytates and their mixtures in a pH range of 6 to 8 may generally be selectively used depending upon the purposes of pharmaceutics as well as functional diets because of their strong acidity.

The number of moles of various bases required to regulate one mole of phytic acid to pH 6 to 8 is shown in Table 1.

TABLE 1

| Bases | pH 6.00 | pH 7.00 | pH 8.00 |
|---|---|---|---|
| NaOH | 7.34 | 8.21 | 8.94 |
| KOH | 7.34 | 8.23 | 8.94 |
| LiOH | 7.41 | 8.38 | 9.30 |
| $NH_4OH$ | 7.61 | 8.55 | 9.45 |
| $HOC_2HCH_2NH_2$ | 7.72 | 8.68 | 9.52 |
| $(HOCH_2CH_2)_2NH$ | 7.54 | 8.45 | 9.31 |
| $(HOCH_2CH_2)_3N$ | 7.20 | 8.53 | 12.1 |
| N-Methylglucamine | 7.62 | 8.49 | 9.25 |
| L-Arginine | 7.79 | 8.67 | 9.6 |
| L-Lysine | 8.01 | 8.98 | 10.0 |
| L-Histidine | 11.3 | — | — |

Phytic acid and its salt are so tasteless and odorless that their oral administration is easily achieved. Thus, the pharmaceutical compositions according to the present invention may be administrated by mixing with drinking water for humans and animals or sprinkling over or blending with dishes and feed in the form of powders or granules.

The pharmaceutical compositions according to the present invention are effective for remedying or treating obesity and hyperlipemia, since they serve to promote the metabolism of fats, to cure coprostasis and diarrhea and to promote the absorption of nutrients such as vitamins.

Further, the compositions according to the present invention may be used as pharmaceutics alone, but may be added to food and diets for increased nutrition.

Still further, the desired effects of the compositions of the present invention are easily obtained by oral administration, since they contain phytic acid and its salt(s) as the main component.

Still further, the compositions of the present invention may be adminphytic acid and its salt(s) are effective.

Still further, the compositions of the present invention are of safety so high that they are continuously usable and are effective for the inhibition of obesity by their continued use or administration.

The present invention will now be explained in detail with reference to the following examples, which are given for the purpose of illustration alone.

EXAMPLE I

Composition a

Twenty-nine (29) g of sodium hydroxide and a suitable amount of refined water are added to 660 g of phytic acid (as an anhydride) to obtain a liquid regulated to pH 6.

Composition b

Four hundred and twelve (412) g of potassium hydroxide and a suitable amount of refined water are added to 660 g of phytic acid (as an anhydride) to obtain a liquid regulated to pH 6.

Composition c

One hundred and seventy-seven (177) g of lithium hydroxide and a suitable amount of refined water are added to 660 g of phytic acid (as an anhydride) to obtain a liquid regulated to pH 6.

Composition d

Five hundred and eighty-one (581) g of ethanolamine and a suitable amount of refined water are added to 660 g of phytic acid (as an anhydride) to obtain a liquid regulated to pH 8.

Composition e

Nine hundred and seventy-nine (979) g of diethanolamine and a suitable amount of refined water are added to 660 g of phytic acid (as an anhydride) to obtain a liquid regulated to pH 8.

Composition f

One thousand eight hundred and five (1805) g of triethanolamine and a suitable amount of refined water are added to 660 g of phytic acid (as an anhydride) to obtain a liquid adjusted to pH 8.

Composition g

One thousand six hundred and fifty-seven (1657) g of N-methylglucamine and a suitable amount of refined water are added to 660 g of phytic acid (as an anhydride) to obtain a liquid adjusted to pH 7.

Composition h

One thousand five hundred and ten (1510) g of L-arginine and a suitable amount of refined water are added to 660 g of phytic acid (as an anhydride) to obtain a liquid adjusted to pH 7.

Composition i

One thousand seven hundred and fifty-three (1753) g of L-histidine and a suitable amount of refined water are added to 660 g of phytic acid (as an anhydride) to obtain a liquid adjusted to pH 6.

Composition j

One hundred and sixteen (116) g of sodium hydroxide, 478 g of potassium hydroxide, 6.08 g of potassium chloride (as a dihydrate), 157 g of disodium hydrogen phosphate (as an anhydride) and a suitable amount of refined water are added to 660 g of phytic acid (as an anhydride) to obtain a liquid adjusted to pH 9.

These compositions a to j may be powderized by crystallization or the addition of a vehicle.

These compositions a to j may also be formed into compositions in the form of liquids or powders, from which the preparations may be obtained.

EXAMPLE 3

The composition j obtained in Example 2 was formed into a composition, from which various preparations were obtained.

Composition A for Preparations

Lactose is added to the composition j (containing 200 mg of phytic acid) to obtain a total of 1000 mg of a composition.

Composition B for Preparations

Lactose is added to the composition j (containing 100 mg of phytic acid) to obtain a total of 1000 mg of a composition.

Composition C for Preparations

Refined water is added to the composition j (containing 100 mg of phytic acid) to obtain a total of 1000 mg of a composition.

Composition D

Light silicic anhydride is added to the composition j (containing 200 mg of phytic acid), followed by drying, which gives a total of 1000 mg of a composition.

PRODUCTION EXAMPLES OF PREPARATIONS

Production Example 1 (Erixir)

| | |
|---|---|
| Composition C | 100 g (10 g calculated as phytic acid) |
| Compound orange extract | 24 ml |
| Ethanol | 400 ml |
| Glycerine | 400 ml |
| Refined water Total: | 1000 ml |

Predetermined amounts of the aforesaid components are uniformly mixed together to obtain a colorless and clear erixir preparation. A five-milliliter dosage of this erixir preparation contains 50 mg of phytic acid.

Production Example 2 (Capsule)

| | |
|---|---|
| Composition A | 200 mg (40 mg calculated as phytic acid) |
| Lactose | 20 mg |
| Corn starch | 38 mg |
| Magnesium stearate | 2 mg |

Predetermined amounts of the aforesaid components are uniformly mixed together and packed in No. 2 capsules. One such capsule contains 40 mg of phytic acid.

Production Example 3 (Granule)

| | |
|---|---|
| Composition A | 600 mg (120 mg calculated as phytic acid) |
| Lactose | 140 mg |
| Corn starch | 250 mg |
| Hydroxypropyl-cellulose | 10 mg |

Predetermined amounts of the aforesaid components are uniformly mixed together, and the mixture is then wet-granulated with water and ethanol into granules. One hundred and twenty (120) mg of phytic acid are contained in an one-gram dosage of such granules.

Production Example 4 (Powder)

The composition A is divided and heat-sealed in aluminium to obtain wrappers each of 1.5 g.

Production Example 5 (Tablet)

| | |
|---|---|
| Composition A | 100 mg (20 mg calculated as phytic acid) |
| Corn starch | 19 mg |
| Crystalline cellulose | 30 mg |
| Magnesium stearate | 1 mg |

Predetermined amounts of the aforesaid components are uniformly mixed together, and the mixture is then compressed into tablets each of 7 mm in diameter and 150 mg in weight. One such tablet contains 20 mg of phytic acid.

Production Example 6 (Syrup)

| | |
|---|---|
| Composition C | 50 g (5 g calculated as phytic acid) |
| White sugar | 300 g |
| D-sorbitol (70%) | 250 g |
| Methyl p-oxybenzoate | 0.3 g |
| Propyl p-oxybenzoate | 0.15 g |
| Sodium citrate | 10 g |
| Perfume | 1.5 g |
| Refined water Total: | 1000 ml |

Predetermined amounts of the aforesaid components are dissolved and mixed together into a colorless and clear syrup. One hundred (100) mg of phytic acid is contained in a twenty-milliliter dosage of this syrup.

Production Example 7 (Dry syrup)

| | |
|---|---|
| Composition B | 100 mg (10 mg calculated as phytic acid) |
| Sodium citrate | 2.4 mg |
| Citric anhydride | 2.2 mg |
| Tragacanth powders | 2.7 g |
| White sugar | suitable amount |
| Hydroxypropyl-cellulose | 3.0 mg |
| Perfume | slight amount |
| Perfume | slight amount |

Predetermined amounts of the aforesaid components are uniformly mixed together, and are then wet-granulated with water and ethanol into a dry syrup. An one (1)-gram dosage of this syrup contains 10 mg of phytic acid.

Production Example 8 (Troche)

| | |
|---|---|
| Composition A | 100 mg (20 mg calculated as phytic acid) |
| White sugar | 870 mg |
| Lactose | 20 mg |
| Magnesium stearate | 10 mg |

Of the aforesaid components the composition A and white sugar are uniformly mixed together in the respective amounts of 100 g and 870 g, and are then wet-granulated with water and ethanol, followed by drying at a temperature of lower than 35° C. Added to the dried product are 20 g of lactose and 10 g of magnesium stearate to obtain troches each of 15 mm in diameter and 1 g in weight. One such troche contains 20 mg of phytic acid.

Production Example 9 (Candy)

| | |
|---|---|
| Composition B | 100 mg (10 mg calcuated as phytic acid) |
| White sugar | 2400 mg |
| Starch syrup | 1500 mg |
| Perfume | slight amount |

Of the aforesaid components, 240 g of white sugar and 150 g of starch syrup are mixed with 100 g of refined water. After melting by heating, the mixture is sieved out for the removal of foreign matters. The resulting liquid is concentrated under pressure with the application of heat for dehydration to prepare a starch syrup dough having a moisture content of 2 to 3% at 130° to 150° C. Added to this dough are 10 g of the composition B and a slight amount of perfume, and the product is molded to obtain candies each of 4 g in weight. Each candy contains 10 mg of phytic acid.

Production Example 10 (Limonada)

| Composition C | 3 g (300 mg calculated as phytic acid) |
|---|---|
| Syrup | 2.5 ml |
| Refined water Total: | 30 ml |

Predetermined amounts of the aforesaid components are uniformly mixed together into limonadas. A thirty (30)-milliliter dosage of such limonadas contains 300 mg of phytic acid.

Production Example 11 (Granule)

| Composition D | 500 mg (100 mg calculated as phytic acid) |
|---|---|
| Garlic powders | 750 mg |
| Lactose | suitable amount |

Predetermined amounts of the aforesaid components are uniformly mixed together, and are then wet-granulated with water and ethanol into granules. One hundred (100) mg of phytic acid is contained in an 1.5-gram dosage of such granules.

Production Example 12 (Drinkable Solution)

| Composition C | 1 g (100 mg calculated as phytic acid) |
|---|---|
| Mel | 0.5 g |
| White sugar | 2.0 g |
| Citric acid | suitable amount |
| Sodium citrate | suitable amount |
| Peppermint | slight amount |
| Refined water | suitable amount |

Predetermined amounts of the aforesaid components were uniformly mixed together into a colorless and clear internal liquid preparation. A thirty (30)-milliliter dosage of this liquid preparation contains 100 mg of phytic acid.

Production Example 13 (Garlic Flavoring)

| Composition D | 0.285 g (0.1 g calculated as phytic acid) |
|---|---|
| Avisel | 0.18 g |
| Garlic powders | 0.75 g |
| Light silicic anhydride | 0.256 g |
| Corn starch | suitable amounts |

Predetermined amounts of the aforesaid components are granulated by a conventional method.

EXAMPLE III

Stability Testing

The preparations according to Production Examples 1 to 10 were subjected to stability testing to measure the amount of residual phytic acid. The results are set forth in Table 2.

TABLE 2

Amounts of Resiudal Phytic Acid in the Stability Testing of the Preparations According to the Production Examples (% with respect to the specified contents)

| Samples | Storage Vessels | At the beginning of Storage | After 3 weeks at 60° C. |
|---|---|---|---|
| P. Ex. 1A* | Glass Bottle | 100.5 | 101.2 |
| P. Ex. 2B* | PTP | 101.4 | 99.4 |
| P. Ex. 3C* | Aluminium Wrapper | 100.1 | 100.0 |
| P. Ex. 4D* | " | 100.9 | 102.1 |
| P. Ex. 5E* | PTP | 99.2 | 99.8 |
| P. Ex. 6F* | Glass Bottle | 102.1 | 100.3 |
| P. Ex. 7G* | Aluminium Wrapper | 100.6 | 100.1 |
| P. Ex. 8H* | Aluminium SP | 99.7 | 100.5 |
| P. Ex. 9I* | Aluminium Bag | 99.9 | 99.2 |
| P. Ex. 10J* | Glass Bottle | 102.1 | 100.9 |
| P. Ex. 11K* | Alminium Wrapper | 100.3 | 100.1 |
| P. Ex. 12L* | Glass Bottle | 100.1 | 99.8 |

A*: Erixir, B*: Capsule, C*: Granule, D*: Powder, E*: Tablet, F*: Syrup, G*: Dry Syrup, H*: Troche, I*: Candy, J*: Limonada, K*: Granule, L*: Drinkable Solution.

EXAMPLE III

Pharmaceutical Effect Test (Induction of Lipoprotein Lipase (LPL for short)

(a) Test Animals and Procedures

In a range of 1 to 50 mg, sodium phytate was administered under anesthesia to four groups of Wistar rats weighing 190 to 200 g and fasted for 12 hours or longer. Five minutes after the administration, blood was gathered from the descending arotae. Sodium citrate was added to the collected blood to regulate its final concentration to 3 mg/ml, which was in turn centrifuged to obtain plasma.

(b) Test Procedures

The activity of LPL in the obtained plasma was determined by the measurement of librating fatty acids.

The free fatty acids were measured with NEFAC Test Wako-Kit (put by Wako Junyaku Co., Ltd. on the market).

(c) Test Results

1) The results of changes in the free fatty acids with changes in the dosage are shown in FIG. 1.

By measurement, it has been found that the free fatty acids are induced depending upon the amount of sodium phytate in the range of 1 to 50 mg/kg/weight, but the animals are killed down in a dosage exceeding 50 mg/kg/weight.

2) Results of Induction-with-time of Free Fatty Acids

Figure 2:
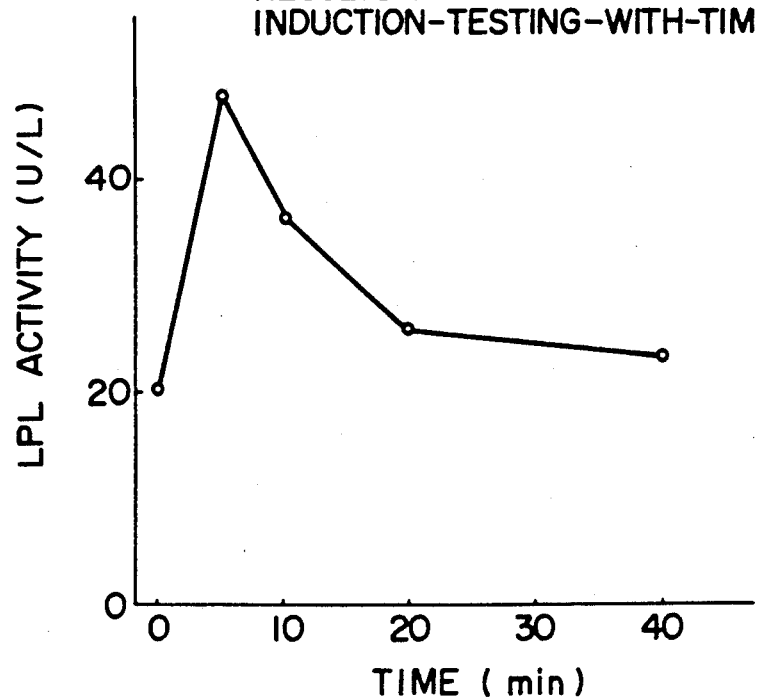
FIG. 2 is a graphical view illustrating the results of induction-testing-with-time of free fatty acids after the administration of phytic acid.

With an intravenous injection of sodium phytate in an dosage of 20 mg/kg/weight, the maximum induction of LPL occurred five minutes after the injection, and was sustained over about 40 minutes, as can be understood from the results shown in FIG. 2.

From the foregoing results, it has been found that the present compositions are effective to lower lipid levels.

Pharmaceutical Effect Test 2 (Weight Reductions)

50, 100 and 150 mg/kg of sodium phytate were intra-peritoneally administered to test groups, 13 and 14 mice weighing about 26 g per group, once a day for 6 days, and physiological saline alone was administered to a control group of 11 mice of the same weight.

The results, as shown in Table 3, have indicated that there are reductions in the weight and such reductions are noticeable in a dosage of 150 mg/kg.

TABLE 3

Reductions in the Weight of Mice

| | Dosage (mg/kg i.p.) | Number of Mice | Day of Administration | Weight 1st Day | 6th Day |
|---|---|---|---|---|---|
| Control Group | | 11 | 26.7 ± 0.5 | 27.5 ± 0.5 | 29.8 ± 0.6 |
| Test Groups | 50 | 14 | 26.2 ± 0.4 | 26.7 ± 0.4 | 29.1 ± 0.4 |
| | 100 | 14 | 26.1 ± 0.3 | 26.3 ± 0.4 | 28.7 ± 0.4 |
| | 150 | 13 | 26.1 ± 0.4 | 26.0 ± 0.4 | 27.6 ± 0.4 |

Pharmaceutical Effect Test 3—(Inhibition of Propagation of Fat Cells of Mice)

Skin cells of a mouse just after birth were collected after decapitation, and a culture liquid was added thereto for 2-day cultivation in a Schale (a laboratory dish). On the third day, an additional culture liquid was provided and, at the same time, sodium phytate was added to a test group at a concentration of 100 ug/ml to observe under a microscope changes in the skin and fat cells on the daily base from the third day after incubation.

From the results, it has been found that the fat cells of the control group show an increase in the amount of fat, but the fat cells of the test group tend to decrease in the amount of fat. In both the test and control groups, any change in the skin cells is not found, which means that the toxicity of sodium phytate makes no contribution to the reduction in the fat cells.

EXAMPLE IV

Organoleptical Tests

Organoleptical Comparison Test 1

For organoleptic comparison testing on whether the taste, edibleness and the smell are good or bad, beefsteaks cooked with 0.5 g (33 mg calculated as phytic acid) of the garlic flavoring preparation according to Production Example 13 and other seasonings were fed to a 20-member panel simultaneously with those without phytic acid. The results are shown in Table 4.

TABLE 4

| | Indistinguishable from phytic acid-free steaks | Better than phytic acid-free steaks | Bad |
|---|---|---|---|
| Taste | 6 | 14 | 0 |
| Edibleness | 5 | 15 | 0 |
| Smell | 1 | 19 | 0 |

From the above results, it has been found that phytic acid excels in the taste, edibleness and the smell, and is effective as a food flavoring material.

Organoleptic Test 2

Thirty (30) ml (100 mg calculated as phytic acid) of the drinkable solution of Production Example 12 was continuously administered to three patients suffering from diabetic hyperlipemia once a day for 7 days, and a questionnaire was conducted on its drinkability and effects. The results are shown in Table 5.

TABLE 5

| | | Good | Indistinguishable |
|---|---|---|---|
| Drinkability | | 3 | 0 |
| Effects | (a) Recovery from fatigue | 2 | 1 |
| | (b) Amelioration of conditions | 3 | 0 |

It is here to be noted that this drinkable solution was administered to the patients, while suggesting that it was a healthful diet effective for diabetes. Although it may not be possible to deduce from such results any significant comment on the workings of phytic acid, it is believed that phytic acid is organoleptically effective as one of food additives.

What is claimed is:

1. A method of treatment for obesity and hyperlipemia symptoms comprising the oral administration to a mammal in need of such treatment of an effective dosage of a pharmaceutical composition consisting essentially of at least one compound selected from the group consisting of phytic acid, a non-toxic phytate salt, and mixtures thereof, and a pharmaceutically acceptable carrier.

2. A method of treatment for obesity and hyperlipemia symptoms according to claim 1, wherein said symptom is Type I hyperlipemia.

3. A method of treatment for obesity and hyperlipemia symptoms according to claim 1, wherein said symptom is a arteriosclerosis.

4. A method of treatment for obesity and hyperlipemia symptoms according to claim 1, wherein said obesity symptoms are selected from the group consisting of fatty liver, diabetes, and macromastia.

5. A method of treatment for obesity and hyperlipemia symptoms according to claim 1, wherein said effective dosage is 1 to 100 mg/kg/day calculated as phytate ion.

6. A method of treatment for obesity and hyperlipemia symptoms according to claim 1, wherein said phytate salt is selected from the group consisting of non-toxic metal salts, amine salts, non-toxic salts with an organic base, basic amino acids and alcohols.

7. A method of treatment for obesity and hyperlipemia symptoms according to claim 6, wherein said phytate salt is selected from the group consisting of potassium phytate, sodium phytate, iron phytate, ammonium phytate, arginine phytate, ornithine phytate, monoethanolamine phytate, diethanolamine phytate, diethylamine phytate, triethanolamine phytate and glucosamine phytate.

8. A method of treatment for obesity and hyperlipemia symptoms according to claim 7, wherein said phytate salt is an iron salt.

* * * * *